US011835515B2

(12) United States Patent
Berg et al.

(10) Patent No.: US 11,835,515 B2
(45) Date of Patent: Dec. 5, 2023

(54) METHOD FOR EVALUATING SUITABILITY OF LIGHTING CONDITIONS FOR DETECTING AN ANALYTE IN A SAMPLE USING A CAMERA OF A MOBILE DEVICE

(71) Applicant: Roche Diabetes Care, Inc., Indianapolis, IN (US)

(72) Inventors: Max Berg, Mannheim (DE); Fredrik Hailer, Mannheim (DE); Timo Klein, Mannheim (DE); Bernd Limburg, Mannheim (DE); Christian Melchinger, Mannheim (DE); Volker Tuerck, Berlin (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 32 days.

(21) Appl. No.: 17/118,185

(22) Filed: Dec. 10, 2020

(65) Prior Publication Data
US 2021/0088506 A1   Mar. 25, 2021

Related U.S. Application Data

(63) Continuation of application No. PCT/EP2019/064675, filed on Jun. 5, 2019.

(30) Foreign Application Priority Data

Jun. 11, 2018 (EP) ..................... 18176999

(51) Int. Cl.
*G01N 33/52* (2006.01)
*G01N 21/77* (2006.01)

(52) U.S. Cl.
CPC .......... *G01N 33/526* (2013.01); *G01N 21/77* (2013.01); *G01N 2021/7759* (2013.01)

(58) Field of Classification Search
CPC ... G01N 2021/7759; G01N 2021/8887; G01N 21/77; G01N 21/8483; G01N 21/8806; G01N 33/526
See application file for complete search history.

(56) References Cited

U.S. PATENT DOCUMENTS 8,877,140 B2    11/2014  Chen et al.
2002/0117639 A1  8/2002  Paolini et al.
(Continued)

FOREIGN PATENT DOCUMENTS

EP    1 801 568 A1    6/2007
EP    1 963 828 B1    3/2010
(Continued)

OTHER PUBLICATIONS

International Preliminary Report on Patentability, PCT/EP2019/064675, dated Sep. 25, 2020, 11 pages.
(Continued)

*Primary Examiner* — Christine T Mui
*Assistant Examiner* — Kathryn Elizabeth Limbaugh
(74) *Attorney, Agent, or Firm* — Bose McKinney & Evans LLP

(57) ABSTRACT

A method of evaluating suitability of lighting conditions for detecting an analyte in a sample using a mobile device camera. A test strip is provided for detecting the analyte. A first image of the test strip is captured while an illumination source of the mobile device is turned off and a second image of the test strip is captured while the illumination source is turned on. A sample is applied to the test strip and the first and second images are compared to thereby determine the difference in lighting conditions between the first image and the second image. The comparison is used to derive information on suitability of the lighting conditions for analyte detection. The lighting conditions are indicated as suitable (Continued)

when a predetermined threshold amount of light intensity used for illumination of the test strip originates from the illumination source.

18 Claims, 6 Drawing Sheets

(56) References Cited

U.S. PATENT DOCUMENTS

| | | | |
|---|---|---|---|
| 2010/0110439 A1 | 5/2010 | Gruler et al. | |
| 2012/0189509 A1 | 7/2012 | Hsiao | |
| 2012/0249779 A1* | 10/2012 | Ji | G01N 21/8806 348/131 |
| 2013/0203043 A1 | 8/2013 | Ozcan et al. | |
| 2013/0273528 A1 | 10/2013 | Ehrenkranz | |
| 2014/0072189 A1 | 3/2014 | Jena et al. | |
| 2015/0055134 A1 | 2/2015 | Papautsky et al. | |
| 2015/0233898 A1 | 8/2015 | Chen et al. | |
| 2015/0359458 A1 | 12/2015 | Erickson et al. | |
| 2017/0146507 A1 | 5/2017 | Wang et al. | |
| 2018/0031551 A1 | 2/2018 | Karlovac et al. | |
| 2019/0376966 A1* | 12/2019 | Pulitzer | G01N 21/77 |

FOREIGN PATENT DOCUMENTS

| | | |
|---|---|---|
| EP | 2 916 117 A1 | 9/2015 |
| EP | 3 108 244 A1 | 12/2016 |
| JP | 2010-019610 A | 1/2010 |
| JP | 2017-511466 A | 4/2017 |
| TW | 201719145 A | 6/2017 |
| WO | WO 2007/079843 A2 | 7/2007 |
| WO | WO 2012/131386 A1 | 10/2012 |
| WO | WO 2014/025415 A2 | 2/2014 |
| WO | WO 2014/178062 A2 | 11/2014 |
| WO | WO 2015/120819 A1 | 8/2015 |

OTHER PUBLICATIONS

International Search Report and Written Opinion of the International Searching Authority, PCT/EP2019/064675, dated Jun. 27, 2019, 10 pages.
Extended European Search Report, EP 18176999.3, dated Nov. 29, 2018, 8 pages.
Hönes et al., Diabetes Technology and Therapeutics, vol. 10, Supplement 1, 2008, pp. 10-26.
The National Optical Astronomy Observatory (NOAO), Recommended Light Levels, Webpage: https://www.noao.edu/education/QLTkit/ACTIVITY_Documents/Safety/LightLevels_outdoor+indoor.pdf (5 pages) 2016.

* cited by examiner

METHOD FOR EVALUATING SUITABILITY OF LIGHTING CONDITIONS FOR DETECTING AN ANALYTE IN A SAMPLE USING A CAMERA OF A MOBILE DEVICE

RELATED APPLICATIONS

This application is a continuation of PCT/EP2019/064675, filed Jun. 5, 2019, which claims priority to EP 18 176 999.3, filed Jun. 11, 2018, the entire disclosures of both of which are hereby incorporated herein by reference.

BACKGROUND

This disclosure refers to a method for evaluating a suitability of lighting conditions for detecting an analyte in a sample using a camera of a mobile device and a detection method for detecting an analyte in a sample by using a camera of a mobile device. The disclosure further relates to a computer program with program means for executing the methods according to the disclosure. Further, the disclosure refers to a mobile device. Methods, computer programs and mobile devices according to the present disclosure may be used in medical diagnostics, in order to qualitatively or quantitatively detect one or more analytes in one or more body fluids. Other fields of application of the present disclosure, however, are possible.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary.

Generally, devices and methods known to the skilled person make use of test elements comprising one or more test chemistries, which, in the presence of the analyte to be detected, are capable of performing one or more detectable detection reactions, such as optically detectable detection reactions. With regard to these test chemistries, reference may be made, e.g., to J. Hoenes et al.: The Technology Behind Glucose Meters: Test Strips, Diabetes Technology & Therapeutics, Volume 10, Supplement 1, 2008, S-10 to S-26. Other types of test chemistry are possible and may be used for performing the present disclosure.

In analytical measurements, specifically analytical measurements based on color formation reactions, one technical challenge resides in the evaluation of the color change which is due to the detection reaction. Besides using dedicated analytical devices, such as handheld blood glucose meters, the use of generally available electronics such as smart phones and portable computers has become more and more popular over the recent years. WO 2012/131386 A1 discloses a testing apparatus for performing an assay, the testing apparatus comprising: a receptacle containing a reagent, the reagent being reactive to an applied test sample by developing a color or pattern variation; a portable device, e.g., a mobile phone or a laptop, comprising a processor and an image capture device, wherein the processor is configured to process data captured by the image capture device and output a test result for the applied test sample.

WO 2014/025415A2 discloses a method and device for performing color-based reaction testing of biological materials. The method includes capturing and interpreting digital images of an unexposed and later exposed instrument within an automatically calibrated environment. The instrument includes a Unique Identification (UID) label, Reference Color Bar (RCB) providing samples of standardized colors for image color calibration, and several test specific sequences of Chemical Test Pads (CTP). The method further includes locating the instrument in the image, extracting the UID, extracting the RCB, and locating the plurality of CTP in each image. The method further reduces image noise in the CTP and calibrates the image automatically according to lighting measurements performed on the RCB. The method further determines test results by comparing the color of the CTP image to colors in a Manufacturer Interpretation Color Chart (MICC). The method shows these results in graphical or quantified mode.

EP 1801568 A1 discloses a test strip and method for measuring analyte concentration in a biological fluid sample. The method involves positioning a camera at a test strip for pictorially detecting a color indicator and a reference color area. A measured value is determined for the relative position between the camera and the strip and compared with a desired value area. The camera is moved to reduce deflection relative to the strip during the deflection between the measured value and the desired value. An image area assigned to the indicator is localized in a colored image that is detected by the camera. An analyte concentration is determined in a sample by a comparison value.

EP 1963828 B1 discloses a method for measurement of the concentration of at least one analyte which is contained in a sample of a biological fluid, a) wherein a test strip is prepared, which has at least one test point, at least one time indicator and at least one reference color range which comprises the color white and/or a color scale, b) wherein the fluid sample is brought into contact with the test point and the time indicator, c) wherein a color indicator is arranged at the test point as a function of the concentration of the analyte, d) wherein the color of the time indicator is changed as a function of the time duration for which the fluid has been brought into contact with the test point and independently of the concentration of the at least one analyte, e) wherein a camera is positioned on the test strip, f) wherein at least one measured value for the relative position between the camera and the test strip is determined, and is compared with a nominal value range, g) wherein, if there is a discrepancy between the measured value and the nominal value range, the camera is moved relative to the test strip in order to reduce the discrepancy, and steps f) and g) are repeated, h) wherein the camera is used to record a color image on which at least the color indicator, the time indicator and the reference color range are imaged, j) wherein the image areas which are associated with the color indicator, the time indicator and the reference color range are localized in the color image, and the color values of these image areas are determined, k) wherein the time duration between the fluid sample being brought into contact with the test point and the recording of the color image is determined on the basis of the color value determined for the time indicator, with the aid of predetermined reference values, and l) wherein the analyte concentration in the sample is determined on the basis of the color values determined for the color indicator and the reference color range and on the basis of the time duration, with the aid of predetermined comparison values.

Reliability and accuracy of the analytical measurement using mobile computing devices generally depends on a large number of technical factors. Specifically, a large number of mobile devices having cameras are available on the market, all having different technical and optical properties which have to be considered for the analytical measurement.

WO 2007/079843 A2 describes a method for measuring a concentration of an analyte contained in a sample of a biological fluid. In said method, a test strip is provided which comprises at least one test point and at least one reference color section encompassing the color white and/or a color scale. The fluid sample is brought in contact with the test point, and a color indicator is disposed on the test point in accordance with the concentration of the analyte. A camera is placed on the test strip. At least one measured value is detected for the relative position between the camera and the test strip and is compared to a set value range. If the measured value deviates from the set value range, the camera is moved relative to the test strip to reduce the deviation. A colored image on which at least the color indicator and the reference color section are represented is detected with the aid of the camera. The image areas assigned to the color indicator and the color matching section are located, and the color values of said image areas are determined. The analyte concentration in the sample is determined based on the color values with the aid of predefined comparative values. EP 3 108 244 A1 and WO 2015/120819 A1 describe a test strip module including a case, a test strip in the case, and a position anchor extending down past a mating surface to a face of a mobile computing device. The position anchor has a shape matching a feature on the face of the mobile computing device.

U.S. Publication No. 2015/233898 A1 describes a test strip module which includes a case, a test strip in the case, and a position anchor extending down past a mating surface to a face of a mobile computing device. The position anchor has a shape matching a feature on the face of the mobile computing device.

Despite the advantages involved in using mobile computing devices for the purpose of performing an analytical measurement, several technical challenges remain. Specifically, reliability and accuracy of the measurements need to be enhanced and ensured. Reliability and accuracy of the analytical measurement may significantly depend on lighting conditions during capturing of images of a test strip for analytical measurement when using the camera of a mobile phone. Specifically, ambient light may have a significant impact on the lighting conditions, for example, due to various illumination means being present at different specific locations and/or depending where the image is captured and whether the image is captured during day or night. Particularly, ambient light may interfere with evaluation of the color formed on a reagent field of a test strip.

It is therefore desirable to provide methods and devices which address the above-mentioned technical challenges of analytical measurements using mobile devices such as consumer-electronics mobile devices, specifically multipurpose mobile devices which are not dedicated to analytical measurements such as smart phones or tablet computers. Specifically desirable are methods and devices which ensure reliability and accuracy of the measurements.

SUMMARY

This disclosure teaches a method for evaluating suitability of lighting conditions for detecting an analyte in a sample using a camera of a mobile device, a detection method for detecting an analyte in a sample by using a camera of a mobile device method, a computer program and a mobile device with the disclosed features. Advantageous embodiments which might be realized in an isolated fashion or in any arbitrary combinations are also disclosed.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "image," "test strip," and "test field," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a method for evaluating a suitability of lighting conditions for detecting an analyte in a sample using a camera of a mobile device is disclosed. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed.

The method comprises the following steps:

a) capturing at least one first image of at least one test strip, wherein the test strip is adapted for detecting the analyte in the sample, the test strip having at least one test field comprising at least one test chemical for performing an optical detection reaction in the presence of the analyte, wherein, during the capturing of the first image, an illumination source of the mobile device is turned off;

b) capturing at least one second image of the test strip, wherein, during the capturing of the second image, the illumination source of the mobile device is turned on;

c) comparing the first and second images captured in steps a) and b), thereby determining a difference in lighting conditions between the first image and the second image; and d) deriving at least one suitability information from the comparison in step c), wherein the suitability information comprises information on a suitability of the lighting conditions for analyte detection.

The term "mobile device" as used herein is a broad term and is to be given its ordinary and customary meaning to a person of ordinary skill in the art and is not to be limited to a special or customized meaning. The term specifically may refer, without limitation, to a mobile electronics device, more specifically to a mobile communication device such as a cell phone or smart phone. Additionally or alternatively, as will be outlined in further detail below, the mobile device may also refer to a tablet computer or another type of portable computer having at least one camera.

The term "test strip" as used herein is a broad term and is to be given its ordinary and customary meaning to a person of ordinary skill in the art and is not to be limited to a special or customized meaning. The term specifically may refer, without limitation, to an arbitrary element or device configured for performing a color-change detection reaction. The test strip may particularly have a test field containing at least one test chemical for detecting the at least one analyte. The test strip, as an example, may comprise at least one substrate, such as at least one carrier, with the at least one test field applied thereto or integrated therein. As an example, the at least one carrier may be strip-shaped, thereby rendering the test element a test strip. These test strips are generally widely in use and available. One test strip may carry a single test field or a plurality of test fields having identical or different test chemicals comprised therein. The test strip may have at least one sample applied thereto.

As further used herein, the term "test field" is a broad term and is to be given its ordinary and customary meaning to a person of ordinary skill in the art and is not to be limited to a special or customized meaning. The term specifically may refer, without limitation, to a coherent amount of the test chemical, such as to a field, e.g., a field of round, polygonal or rectangular shape, having one or more layers of material, with at least one layer of the test field having the test chemical comprised therein. Other layers may be present providing specific optical properties such as reflective properties, providing spreading properties for spreading the sample or providing separation properties such as for separating of particulate components of the sample, such as cellular components.

The term "test chemical" as used herein is a broad term and is to be given its ordinary and customary meaning to a person of ordinary skill in the art and is not to be limited to a special or customized meaning. The term specifically may refer, without limitation, to a chemical compound or a plurality of chemical compounds such as a mixture of chemical compounds suited for performing a detection reaction in the presence of the analyte, wherein the detection reaction is detectable by specific means, such as optically. The detection reaction specifically may be analyte-specific. The test chemical, in the present case, specifically may be an optical test chemical, such as a color-change test chemical which changes in color in the presence of the analyte. The color change specifically may depend on the amount of analyte present in the sample. The test chemical, as an example, may comprise at least one enzyme, such as glucose oxidase and/or glucose dehydrogenase. Additionally, other components may be present, such as one or more dyes, mediators and the like. Test chemicals are generally known to the skilled person and reference may be made to J. Hones et al.: Diabetes Technology and Therapeutics, Vol. 10, Supplement 1, 2008, pp. 10-26. Other test chemicals, however, are feasible, too.

The term "analyte" as used herein is a broad term and is to be given its ordinary and customary meaning to a person of ordinary skill in the art and is not to be limited to a special or customized meaning. The term specifically may refer, without limitation, to one or more specific chemical compounds and/or other parameters to be detected and/or measured. As an example, the at least one analyte may be a chemical compound which takes part in metabolism, such as one or more of glucose, cholesterol or triglycerides. Additionally or alternatively, other types of analytes or parameters may be determined, e.g., a pH value.

The term "detecting an analyte in a sample" as used herein is a broad term and is to be given its ordinary and customary meaning to a person of ordinary skill in the art and is not to be limited to a special or customized meaning. The term specifically may refer, without limitation, to a quantitatively and/or qualitatively determination of at least one analyte in an arbitrary sample. For example, the sample may comprise a body fluid, such as blood, interstitial fluid, urine, saliva or other types of body fluids. The result of the analytical measurement, as an example, may be a concentration of the analyte and/or the presence or absence of the analyte to be determined. Specifically, as an example, the analytical measurement may be a blood glucose measurement, thus the result of the analytical measurement may, for example, be a blood glucose concentration.

The term "suitability" may refer, without limitation, to a property of an element or device for performing one or more predetermined functions and to appropriateness of ambient conditions for ensuring reliability and accuracy of detecting the analyte in the sample. Thus, the term refers to one or both of properties of the device and ambient conditions. The suitability may be qualified and/or quantified by determining whether a predetermined requirement is fulfilled. The predetermined requirement, for example at least one threshold, may be derived, as an example, from experiments or from boundary conditions determined, e.g., by the precision to be achieved. The term "suitability information" may refer, without limitation, to an indication or information regarding the suitability, specifically in the present case of the suitability of lighting conditions for the purpose of performing the analytical measurement. The item of suitability information, as an example, may be Boolean or digital information, such as indicating "suited" or "not suited"/"unsuited." Additionally or alternatively, however, the suitability information may comprise a quantitative result, such as a degree of suitability. For example, the suitability information may comprise information about sufficiency of light intensity originating from the illumination source of the mobile device for illuminating the test strip. Specifically, the suitability information may comprise information about sufficiency of light intensity originating from the illumination source of the mobile device for illuminating the test strip in relation to and/or in comparison to ambient light intensities and/or ambient light conditions.

As used herein, the term "evaluating a suitability of lighting conditions" refers to testing and/or determining and/or assessing and/or estimating lighting conditions. As used herein, the term "lighting conditions" refers to image capturing conditions, specifically both of ambient light conditions and light intensities provided by the illumination source of the mobile device. The term "lighting conditions" furthermore refers to reflection conditions, in particular reflections properties of the test strip, for example due to material of the test strip. The terms "ambient light" or "ambient light conditions" refer to light from available natural or artificial light sources illuminating the test strip independent from the illumination provided by the illumination source of the mobile device. The ambient light may be generated and/or provided by artificial light sources such as room light, e.g., lamps, and/or natural light sources such as the sun, the moon, starlight, lightning. The lighting conditions may depend on time, in particular day or night time. The lighting condition may depend on location, in particular if the image is captured outdoor or indoor or on geographical location. In particular for outdoor measurements, the lighting conditions may depend on weather conditions. For indoor measurements, the lighting conditions may depend on room lightings, which may differ dependent on activity such as in homes, supermarkets, theaters, etc.

The term "camera" as used herein is a broad term and is to be given its ordinary and customary meaning to a person of ordinary skill in the art and is not to be limited to a special or customized meaning. The term specifically may refer, without limitation, to a device having at least one imaging element configured for recording or capturing spatially resolved one-dimensional, a two-dimensional or even three-dimensional optical information. As an example, the camera may comprise at least one camera chip, such as at least one CCD chip and/or at least one CMOS chip configured for recording images. For example, the camera may be a color camera, as will be described in detail below, comprising at least three color pixels. The camera may be a color CMOS camera. For example, the camera may comprise black and white pixels and color pixels. The color pixels and the black and white pixels may be combined internally in the camera. The camera may comprise at least one color camera and at least one black and white camera, such as a black and white CMOS. The camera may comprise at least one black and white CMOS chip. The camera generally may comprise a one-dimensional or two-dimensional array of image sensors, such as pixels. As an example, the camera may comprise at least 10 pixels in at least one dimension, such as at least 10 pixels in each dimension. It shall be noted, however, that other cameras are also feasible. The camera may be a camera of a mobile communications device. This disclosure specifically shall be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible. The camera, besides at least one camera chip or imaging chip, may comprise further elements, such as one or more optical elements, e.g., one or more lenses. As an example, the camera may be a fix-focus camera, having at least one lens which is fixedly adjusted with respect to the camera. Alternatively, however, the camera may also comprise one or more variable lenses which may be adjusted, automatically or manually.

The camera specifically may be a color camera. Thus, such as for each pixel, color information may be provided or generated, such as color values for three colors R, G, B. A larger number of color values is also feasible, such as four colors for each pixel. Color cameras are generally known to the skilled person. Thus, as an example, each pixel of the camera chip may have three or more different color sensors, such as color recording pixels like one pixel for red (R), one pixel for green (G) and one pixel for blue (B). For each of the pixels, such as for R, G, B, values may be recorded by the pixels, such as digital values in the range of 0 to 255, depending on the intensity of the respective color. Instead of using color triples such as R, G, B, as an example, quadruples may be used, such as C, M, Y, K or RGGB, BGGR, RGBG, GRGB, RGGB or the like. The color sensitivities of the pixels may be generated by color filters, such as color filter arrays, for example by at least one Bayer filter, or by appropriate intrinsic sensitivities of the sensor elements used in the camera pixels. These techniques are generally known to the skilled person.

As used herein, without limitation, the term "image" specifically may relate to data recorded by using a camera, such as a plurality of electronic readings from an imaging device, such as the pixels of the camera chip. The image itself, thus, may comprise pixels, the pixels of the image correlating to pixels of the camera chip. Consequently, when referring to "pixels", reference is either made to the units of image information generated by the single pixels of the camera chip or to the single pixels of the camera chip directly. The image may comprise raw pixel data. For example, the image may comprise data in the RGGB space, single color data from one of R, G or B pixels, a Bayer pattern image or the like. The image may comprise evaluated pixel data such as a full-color image or an RGB image. The raw pixel data may be evaluated for example by using demosaicing algorithms and/or filtering algorithms. These techniques are generally known to the skilled person.

The term "capturing at least one image" refers to one or more of imaging, image recording, image acquisition, image capturing. The term "capturing at least one image" may comprise capturing a single image and/or a plurality of images such as a sequence of images. The capturing of the at least one image may be initiated by the user action or may automatically be initiated, e.g., once the presence of the at least one object within a field of view and/or within a predetermined sector of the field of view of the camera is automatically detected. These automatic image acquisition techniques are known, e.g., in the field of automatic barcode readers, such as from automatic barcode reading apps.

As used herein, the term "the illumination source of the mobile device" refers to an arbitrary light source of the mobile device. The term "illumination source" refers to at least one device adapted to generate light for illuminating the object. As used herein, the term "light" generally refers to electromagnetic radiation in one or more of the visible spectral range, the ultraviolet spectral range and the infrared spectral range. The term "visible spectral range" generally refers to a spectral range of 380 nm to 780 nm. Preferably, light as used within the present disclosure is light in the visual spectral range. The illumination source may comprise at least one light-emitting diode integrated in the mobile device. In particular, the illumination source may be a backlighting of the mobile device, in particular of the mobile phone. The mobile device may comprise further illumination devices such as at least one illumination source illuminating the display and/or the display may be designed as further illumination source itself.

The illumination source may have two states, an on-state in which it generates a light beam for illuminating the test strip and an off-state in which the illumination source is off. As used herein, the term "is turned on" refers to that the illumination source is activated and/or switched on to illuminate the test strip. The term "is turned off" refers to that the illumination source is within an off-state or is actively switched off. As outlined above, in step a) a first image is captured wherein the illumination source of the mobile device is turned off. This may allow capturing an image comprising light intensities of ambient light sources only and independent from illumination provided by the illumination source of the mobile device. In step b) the illumination source is turned on such that it may be possible to determine the second image comprising illumination intensities from both ambient light and from the illumination by the illumination source of the mobile device.

The illumination source may comprise at least one light-emitting diode (LED) integrated in the mobile device. The illumination source may comprise at least one white light LED. The white light LED may be controlled using a short current pulse such that the white light LED may be adapted to generate a bright flash of light. The illumination source may be adapted to illuminate the test strip all the time during capturing of the image. In contrast to electron flashes, flash duration of the white light LED may take several 100 ms. This may allow that the illumination source illuminates the test strip all the time during capturing of the image in a flash-mode of the LED. Alternatively, the LED may be adapted to be permanently illuminating the test strip in a non-flash mode.

The illumination source may be adapted to outshine in brightness ambient light. The illumination source may be an essentially dominant light source when capturing the image in step b) of the test strip. The term "essentially dominant" refers to the illuminance of the illumination source exceeding illuminance of ambient light, wherein low lighting from ambient light is possible. Illuminance of flashes generated by the white light LED used in mobile devices may be from 80 to 300 lux at an object distance of 1 m. Thus, at an object distance of 0.1 m, illuminance of flashes generated by the white light LED may be from 8000 to 30000 lux. For comparison, full daylight may have 10752 lux, an overcast day may have 1075 lux, a very dark day may have 107 lux, and twilight may have 10.8 lux, see Recommended Light Levels published by the National Optical Astronomy Observatory. The illumination source may be adapted to generate at least one light beam for illuminating the test strip comprising light intensities above light intensities of ambient light. The light intensities of the illumination generated by the illumination source may exceed the light intensities of ambient light by a factor of two, preferably by a factor of 10 and more preferably by a factor of 100.

Step c) comprises comparing the first and second images captured in steps a) and b), thereby determining a difference in lighting conditions between the first image and the second image. As outlined above, each pixel of the camera chip may have three or more different color sensors, such as color recording pixels like one pixel for red (R), one pixel for green (G) and one pixel for blue (B). Each of the color sensors and/or of the color recording pixels may be adapted to generate a single signal or a plurality of sensor signals in response to illumination. The sensor signal may be or may comprise at least one electrical signal, such as at least one analog electrical signal and/or at least one digital electrical signal. Further, either raw sensor signals may be used, or processed or preprocessed sensor signals, such as preprocessed by filtering or the like, may be used. The camera may be adapted to capture the first and second images in steps a) and b) in at least one color channel, in particular at least one color channel selected from the group consisting of R channel, G channel and B channel. The camera may be adapted to capture the first and second images in steps a) and b) in each of the color channels. As used herein, the term "color channel" refers to color recording pixels of the camera chip for the same color. The camera and/or the processor, in particular the processor of the mobile device, may be adapted to determine from the first image at least one first intensity distribution and from the second image at least one second intensity distribution for at least one of the color channels. Preferably, a first intensity distribution and a second intensity distribution may be determined for each of the color channels. For at least one color channel, the camera and/or the processor, in particular the processor of the mobile device, may be adapted to determine from the respective first intensity distribution a first intensity spectrum of the respective color channel and from the respective second intensity distribution a second intensity spectrum of the respective color channel. As used herein, the term "intensity spectrum" refers to an intensity distribution as a function of wavelength. The term "comparing the first and second images" refers to comparing the first intensity distribution and the second intensity distribution of at least one of the color channels and/or comparing the first intensity spectrum and the second intensity spectrum of at least one of the color channels. The comparing may comprise at least one mathematical operation such as subtracting the respective sensor signals generated by the color recording pixels of one color channel and/or subtracting intensity distributions of one color channel and/or subtracting the intensity spectra of one color channel, and/or dividing the respective sensor signals of one color channel and/or dividing the intensity distributions of one color channel and/or dividing the intensity spectra of one color channel. For example, the comparing may comprise determining a difference between the first intensity distribution and the second intensity distribution of at least one of the color channels. Specifically, for the R, G and B channels the difference Δ may be determined by $$\Delta_{color} = I_{color}^{LEDON} - I_{color}^{LEDOFF},$$

with color=R, G, B, wherein $\Delta_{color}$ is the difference in the respective color channel, $I_{color}^{LEDON}$ is the intensity distribution of the second image of the respective color channel and $I_{color}^{LEDOFF}$ is the intensity distribution of the first image of the respective color channel. Additionally or alternatively, the comparing may comprise determining a quotient by dividing the first intensity distribution and the second intensity distribution and/or by dividing multiples and/or dividing linear combinations of the first intensity distribution and the second intensity distribution for at least one of the color channels. Specifically, for the R, G and B channels the quotient may be determined by $$Q_{color} = I_{color}^{LEDON} / I_{color}^{LEDOFF},$$

with color=R, G, B, wherein $Q_{color}$ is the quotient in the respective color channel, $I_{color}^{LEDON}$ is the intensity distribution of the second image of the respective color channel and $I_{color}^{LEDOFF}$ is the intensity distribution of the first image of the respective color channel. The camera and/or the processor in particular the processor of the mobile device, may be adapted to perform the named operations, preferably by using at least one data processing device and, more preferably, by using at least one processor and/or at least one application-specific integrated circuit. Thus, as an example, the mobile device may comprise at least one data processing device having a software code stored thereon comprising a number of computer commands. The mobile device may provide one or more hardware elements for performing one or more of the named operations and/or may provide one or more processors with software running thereon for performing one or more of the named operations. The term "difference" may refer to deviations, in particular in intensity spectrum, of the first and second images. Specifically, the term "difference" refers to deviations above statistical fluctuations. The illumination source of the mobile device may have a known or predetermined spectral composition. The term "spectral composition" refers to an intensity spectrum of the illumination generated by the illumination source. In particular, at least one distribution of light intensities as a function of wavelength for each of the R, G, B channels may be known or predetermined. Specifically, an emission spectrum of the white light LED may be known or may be determined empirically. The spectral composition may be stored in a table or a lookup table and may be determined, e.g., empirically and may, as an example, be stored in at least one data storage device of the mobile device, e.g., by software, specifically by the app downloaded from an app store or the like. Generally, the illuminated test strip may absorb light in a specific wavelength range whereas the non-absorbed light is reflected and captured by the camera. Thus, a spectral characteristic or composition of the light illuminating the test strip may have direct impact on the resulting RGB-values of the captured image. Since the spectral composition of the illumination source is known or is predetermined, it may be possible to determine the amount of light intensity used for illumination of the test strip which originates from the illumination source. The mobile device may comprise at least one processor which may be adapted to compare the first image and the second image.

The first image and the second image may be captured prior to an application of the sample. Additionally or alternatively, the method may comprise at least one sample application step, wherein in the sample application step a sample may be applied to the test strip. Specifically, the sample may be applied to the test strip prior to steps a) and/or b).

Step d) comprises deriving the at least one suitability information from the comparison in step c). The deriving the suitability information in step d) may comprise comparing the difference in lighting conditions determined in step c) with at least one threshold value. Only in case the difference in lighting conditions between the second image and the first image at least equals the threshold value, the suitability information may be set to indicate a suitability of the lighting conditions for analyte detection. The threshold value may depend on ambient light conditions. For example, the user and/or the processor may be adapted to adjust and/or select the threshold value dependent on ambient light conditions. The threshold value may be stored in a table or a lookup table and may be determined, e.g., empirically and may, as an example, be stored in at least one data storage device of the mobile device, e.g., by software, specifically by the app downloaded from an app store or the like. For example, the suitability information may be set to indicate a suitability of the lighting conditions for subsequent analyte detection only in case at least 70% of light intensity used for illumination of the test strip originates from the illumination source. For example, the suitability information may be set to indicate a suitability of the lighting conditions for subsequent analyte detection only in case at least 80% of light intensity used for illumination of the test strip originates from the illumination source. Other thresholds may be possible. For example, the suitability information may be set to indicate a suitability of the lighting conditions for subsequent analyte detection only in case 90% of light intensity used for illumination of the test strip originates from the illumination source.

Light conditions can be indicated as suitable, even in the case of a bright ambient light source, if a composition of the ambient light essentially corresponds to an expected composition of the illumination generated by the illumination source. The term "composition" refers to color composition of the illumination, in particular a composition of intensity distributions of the respective color channels. The term "expected composition" refers to a predetermined spectral composition.

The term "essentially corresponds to" refers to conditions wherein the composition of the ambient light corresponds to the expected composition of the illumination generated by the illumination source with a tolerance of ±30% or less, preferably with a tolerance of ±20% or less, most preferably with a tolerance of ±10% or less. The light conditions may be indicated as suitable if $I_R^{Ambient}/I_G^{Ambient}/I_B^{Ambient} \leq \varepsilon$ $(I_R^{LEDON}/I_G^{LEDON}/I_B^{LEDON})$ is fulfilled, wherein $I_R^{Ambient}$, $I_G^{Ambient}$, $I_B^{Ambient}$ are the intensity distributions of the respective color channels for illumination by ambient light, $I_R^{LEDON}$, $I_G^{LEDON}$, $I_B^{LEDON}$ are the intensity distributions of the respective color channels for illumination generated by the illumination source and $\varepsilon \leq 0.3$, preferably $\varepsilon \leq 0.2$, most preferably $\varepsilon \leq 0.1$.

The method may further comprise checking and/or evaluating whether or not the illumination source provides for sufficient illumination intensity. The checking and/or evaluating whether or not the illumination source is configured for providing sufficient illumination may use at least one threshold method. The sufficiency of the illumination intensity may depend on surface properties of the test strip and/or ambient light conditions. In particular, in case the test strip having high reflection properties lower light intensity may be sufficient compared to dark or low reflection properties. Further, in case of bright ambient light conditions, for example due to sunlight, higher intensity may be required compared to shielded ambient light conditions.

In a further aspect of this disclosure, a detection method for detecting an analyte in a sample by using a camera of a mobile device is disclosed. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. The method comprising the following steps:

i) evaluating lighting conditions by using the method for evaluating a suitability of lighting conditions according to one of the preceding embodiments;

ii) if the suitability information on the suitability of the lighting conditions indicates the lighting conditions to be suitable for analyte detection, performing the following steps:

A) providing at least one test strip for detecting the analyte in the sample, the test strip having at least one test field comprising at least one test chemical for performing an optical detection reaction in the presence of the analyte;

B) applying at least one sample to the test field of the test strip;

C) capturing at least one image of the test field by using the camera, wherein during said capturing the illumination source of the mobile device is turned on; and D) determining, from the image captured in step C), the analyte concentration in the sample.

With respect to embodiments and definition of the detection method reference is made to the description of the method for evaluating a suitability of lighting conditions above and as described in further detail below. In particular, with respect to method step i), reference may be made to the description of the method for evaluating a suitability of lighting conditions above.

The determining of the analyte concentration may comprise an optical detection. As used herein, the term "optical detection" refers to a detection of a reaction using an optical test chemical, such as a color-change test chemical which changes in color in the presence of the analyte. The color change specifically may depend on the amount of analyte present in the sample. Step D) may comprise analyzing the color of a spot on the test field of the test strip, said spot at least partially comprising the sample. Techniques for determining the analyte by optical detection and in particular analyzing color of the spot on the test filed are generally known to the skilled person. For evaluating the at least one image and deriving the at least one analytical information thereof, several algorithms may be used which generally are known to the skilled person in the field of analytics, such as in the field of blood glucose monitoring. Thus, as an example, a color of the test element, such as a color of at least one test field having at least one test chemical, may be evaluated. As an example, when evaluating the image, a region of interest may be defined within the image of the test element, such as a region of interest within a test field of the test element, and an analysis of the color may be performed, such as a statistical analysis. As an example, a rectangular, square, polygonal, oval or circular region of interest may be defined within the part of the image which is recognized to be an image of the test field. Subsequently, a statistical analysis of the color of the pixels within the region of interest may be performed. As an example, one or more color coordinates may be derived for the pixels, and a statistical analysis of the color coordinates may be performed over the region of interest. As an example, the center of the distribution of the at least one color coordinate may be determined. The term "color coordinate" as used herein is a broad term and is to be given its ordinary and customary meaning to a person of ordinary skill in the art and is not to be limited to a special or customized meaning. The term specifically may refer, without limitation, to the coordinate of an arbitrary color coordinate system used for describing a color using coordinates. Several color coordinate systems are generally known to the skilled person and may also be used in the context of this disclosure. Thus, as an example, a colorimetric coordinate system or a coordinate system may be used which is based on the human perception, such as the CIE 1964 color space, the Munsell color system or other coordinate systems, such as R, G, B, L, a, b.

Thus, for deriving the analytical information from the image, as an example, a predetermined or determinable relationship between the at least one color coordinate of the test element, such as the test field, may be monitored. As outlined above, statistical analysis may be performed over the test element or a part thereof, such as over a test field containing the at least one test chemical and/or over a region of interest within the test field containing the at least one test chemical. Thus, as an example, the at least one test field within the image of the test element may be recognized, preferably automatically, e.g., by pattern recognition and/or other algorithms as described in examples below. Again, one or more regions of interest may be defined within the partial image of the test field. Over the region of interest, color coordinates, e.g., again blue color coordinates and/or other color coordinates, may be determined, e.g., again by using one or more histograms. The statistical analysis may comprise fitting one or more fitting curves, such as described above, to the at least one histogram, thereby, e.g., determining a center of a peak. Thus, the color formation reaction may be monitored by using one or more images, wherein, for the one or more images, by using statistical analysis, the center of the peak may be determined, thereby determining a color shift within the at least one coordinate. Once the color formation reaction is finished or has reached a predetermined or determinable endpoint, as the skilled person generally knows, e.g., from blood glucose monitoring, the shift in the at least one color coordinate or an endpoint color coordinates may be determined and may be transformed into, e.g., a concentration of the analyte in the sample by using a predetermined or determinable correlation between the color coordinate and the concentration. The correlation, as an example a transformation function, a transformation table or a lookup table, may be determined, e.g., empirically and may, as an example, be stored in at least one data storage device of the mobile device, e.g., by the software, specifically by the app downloaded from an app store or the like.

In case the evaluating of lighting conditions in step i) is not set to indicate that the lighting conditions are suitable, the mobile device may be adapted to abort and/or to prevent detecting the analyte in the sample. Additionally or alternatively, in case the evaluating of lighting conditions in step i) is not set to indicate that the lighting conditions are suitable, the mobile device may be adapted to generate at least one warning. Additionally or alternatively, in case the evaluating of lighting conditions in step i) is not set to indicate that the lighting conditions are suitable, the mobile device may be adapted to repeat step i). Additionally or alternatively, in case the evaluating of lighting conditions in step i) is not set to indicate that the lighting conditions are suitable, the mobile device may be adapted to generate at least one prompt to the user to change ambient light conditions, for example to move to a different location and/or to switch off disturbing light sources.

After step D) the lighting conditions may be evaluated by using the method for evaluating a suitability of lighting conditions according to this disclosure. The determined analyte concentration may be rejected if the suitability information on the suitability of the lighting conditions indicates the lighting conditions not to be suitable for analyte detection. The mobile device may be adapted to generate a warning to the user, such as a visual warning on a display of the mobile device and/or at least one acoustical warning.

Step C) may comprise providing visual indication for the user to position the test strip relative to the camera such that the test field at least partially is located in a target area. As used herein, the term "target area" refers to a predetermined or pre-specified region in which the test field of the test strip may be supposed to be located during capturing the image. A visual indication such as visual guidance may be given to the user prior to capturing the image. The visual indication may comprise at least one instruction such as a text message and/or a graphical instruction. For example, the visual indication may comprise a visualization of the test strip or parts of the test strip such as a contour and/or outline of the test strip. The visual indication may comprise an outline of the test strip or a reference region on the test strip, for example a frame which corresponds to a shape of the test strip, superimposed on the display of the mobile device, providing visual guidance for positioning the camera relative to the test strip. The capturing of the at least one image may be initiated automatically in case it is determined that the sharpness criterion and/or the spatial criterion may be fulfilled, in particular in case it is determined that the outline of the test strip of the visual indication overlays the test strip. The visual indication may depend on the test strip used. For example, the visual indication such as a contour and/or outline of the test strip may be determined empirical and/or may be stored in at least one lookup table and/or in at least one data storage of the mobile device, e.g., by software, specifically by at least one app downloaded from an app store or the like. Additionally or alternatively, audio guidance or other type of guidance may be given.

As will be outlined in further detail below, the method for evaluating a suitability of lighting conditions and the detection method may fully or partially be computer implemented, specifically on a computer of the mobile device, such as a processor of the mobile device. Thus, specifically, the methods may comprise using at least one processor and software instructions for performing at least method steps c) and d) of the method for evaluating a suitability of lighting conditions and/or method step D) of the detection method. Specifically, the methods may fully or partially be implemented as so-called apps, e.g., for Android or iOS, and may, as an example, be downloadable from an app store. The software instructions, specifically the app, further may provide user instructions, e.g., by one or more of a display, by audio instructions or other instructions, in order to support the method steps of the method for evaluating a suitability of lighting conditions and/or the detection method. Therein, as indicated above, method steps a) and b) may also fully or partially be computer implemented, e.g., by automatically taking the first and second image of the at least one test strip by using the camera once the test strip is within a field of view of the camera and/or within a certain range within the field of view. The processor for performing the method for evaluating a suitability of lighting conditions method and/or the detection method specifically may be part of the mobile device.

As outlined above, the mobile device specifically may be a mobile computer and/or a mobile communications device. Thus, specifically, the mobile device may be selected from the group consisting of: a mobile communications device, specifically a smart phone; a portable computer, specifically a notebook; a tablet computer.

As indicated above, further method steps may be computer implemented or computer assisted, specifically by a processor of the mobile device.

In a further aspect of this disclosure, a computer program including computer-executable instructions for performing the method for evaluating a suitability of lighting conditions according to any one of the embodiments as described herein is disclosed. Specifically the computer-executable instructions may be suited for performing one or more of method steps a), b), c) and d). In particular, the program is executed on a computer or a computer network, specifically on a processor of a mobile device having at least one camera.

Thus, generally speaking, disclosed and proposed herein is a computer program including computer-executable instructions for performing the method for evaluating a suitability of lighting conditions according to this disclosure in one or more of the embodiments enclosed herein when the program is executed on a computer or computer network. Specifically, the computer program may be stored on a computer-readable data carrier. Thus, specifically, one, more than one or even all of method steps as indicated above may be performed by using a computer or a computer network, preferably by using a computer program. The computer specifically may be fully or partially integrated into the mobile device, and the computer programs specifically may be embodied as a software app. Alternatively, however, at least part of the computer may also be located outside the mobile device.

Further disclosed and proposed herein is a data carrier having a data structure stored thereon, which, after loading into a computer or computer network, such as into a working memory or main memory of the computer or computer network, may execute the method for evaluating a suitability of lighting conditions according to one or more of the embodiments disclosed herein, specifically one or more of the method steps mentioned above.

Further disclosed and proposed herein is a computer program product with program code means stored on a machine-readable carrier, in order to perform the method for evaluating a suitability of lighting conditions according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, disclosed and proposed herein is a modulated data signal which contains instructions readable by a computer system or computer network, for performing the method for evaluating a suitability of lighting conditions according to one or more of the embodiments disclosed herein, specifically one or more of the steps of the method for evaluating a suitability of lighting conditions as mentioned above.

Specifically, further disclosed herein are:
- a computer or computer network comprising at least one processor, wherein the processor is adapted to perform the method for evaluating a suitability of lighting conditions according to one of the embodiments described in this description,
- a computer loadable data structure that is adapted to perform the method for evaluating a suitability of lighting conditions according to one of the embodiments described in this description while the data structure is being executed on a computer,
- a computer program, wherein the computer program is adapted to perform the method for evaluating a suitability of lighting conditions according to one of the embodiments described in this description while the program is being executed on a computer,
- a computer program comprising program means for performing the method for evaluating a suitability of lighting conditions according to one of the embodiments described in this description while the computer program is being executed on a computer or on a computer network,
- a computer program comprising program means according to the preceding embodiment, wherein the program means are stored on a storage medium readable to a computer,
- a storage medium, wherein a data structure is stored on the storage medium and wherein the data structure is adapted to perform the method for evaluating a suitability of lighting conditions according to one of the embodiments described in this description after having been loaded into a main and/or working storage of a computer or of a computer network, and a computer program product having program code means, wherein the program code means can be stored or are stored on a storage medium, for performing the method for evaluating a suitability of lighting conditions according to one of the embodiments described in this description, if the program code means are executed on a computer or on a computer network.

In a further aspect of this disclosure, a computer program including computer-executable instructions for performing the detection method according to any one of the embodiments as described herein is disclosed. Specifically the computer-executable instructions may be suited for performing one or more of method steps i) and ii). In particular, the program is executed on a computer or a computer network, specifically on a processor of a mobile device having at least one camera.

Thus, generally speaking, disclosed and proposed herein is a computer program including computer-executable instructions for performing the detection method according to this disclosure in one or more of the embodiments enclosed herein when the program is executed on a computer or computer network. Specifically, the computer program may be stored on a computer-readable data carrier. Thus, specifically, one, more than one or even all of method steps as indicated above may be performed by using a computer or a computer network, preferably by using a computer program. The computer specifically may be fully or partially integrated into the mobile device, and the computer programs specifically may be embodied as a software app. Alternatively, however, at least part of the computer may also be located outside the mobile device.

Further disclosed and proposed herein is a data carrier having a data structure stored thereon, which, after loading into a computer or computer network, such as into a working memory or main memory of the computer or computer network, may execute the detection method according to one or more of the embodiments disclosed herein, specifically one or more of the method steps mentioned above.

Further disclosed and proposed herein is a computer program product with program code means stored on a machine-readable carrier, in order to perform the detection method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, disclosed and proposed herein is a modulated data signal which contains instructions readable by a computer system or computer network, for performing the detection method according to one or more of the embodiments disclosed herein, specifically one or more of the steps of the detection method as mentioned above.

Specifically, further disclosed herein are:

a computer or computer network comprising at least one processor, wherein the processor is adapted to perform the detection method according to one of the embodiments described in this description, a computer loadable data structure that is adapted to perform the detection method according to one of the embodiments described in this description while the data structure is being executed on a computer, a computer program, wherein the computer program is adapted to perform the detection method according to one of the embodiments described in this description while the program is being executed on a computer, a computer program comprising program means for performing the detection method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the detection method according to one of the embodiments described in this description after having been loaded into a main and/or working storage of a computer or of a computer network, and a computer program product having program code means, wherein the program code means can be stored or are stored on a storage medium, for performing the detection method according to one of the embodiments described in this description, if the program code means are executed on a computer or on a computer network.

In a further aspect of this disclosure, a mobile device for performing an analytical measurement is disclosed. The mobile devices comprises:

at least one camera;

at least one illumination source; and at least one processor, comprising program means for performing the method for evaluating a suitability of lighting conditions according to one of the preceding embodiments.

For most of the terms used herein and possible definitions, reference may be made to the description of the methods above.

The processor further may comprise program means for performing the detection method according to any one of the preceding embodiments. The mobile device may be a mobile communications device.

The methods and devices according to this disclosure may provide a large number of advantages over known methods and devices for analytical measurements. This disclosure may improve a reliability and accuracy of the process of performing an analytical measurement, compared to processes known from the art. Specifically, this disclosure may improve the reliability and accuracy of an application, e.g., an app, including computer-executable instructions for performing an analytical measurement, compared to known apps or computer programs. In particular, this disclosure may allow ensuring robust image capturing conditions independent of ambient light conditions and for different mobile devices. Specifically this may be ensured by avoiding and/or significantly reducing the impact of ambient light.

Summarizing and without excluding further possible embodiments, the following embodiments may be envisaged:

Embodiment 1: A method for evaluating a suitability of lighting conditions for detecting an analyte in a sample using a camera of a mobile device, comprising the following steps:

a) capturing at least one first image of at least one test strip, wherein the test strip is adapted for detecting the analyte in the sample, the test strip having at least one test field comprising at least one test chemical for performing an optical detection reaction in the presence of the analyte, wherein, during the capturing of the first image, an illumination source of the mobile device is turned off;
b) capturing at least one second image of the test strip, wherein, during the capturing of the second image, the illumination source of the mobile device is turned on;
c) comparing the first and second images captured in steps a) and b), thereby determining a difference in lighting conditions between the first image and the second image; and
d) deriving at least one suitability information from the comparison in step c), wherein the suitability information comprises information on a suitability of the lighting conditions for analyte detection.

Embodiment 2: The method according to the preceding embodiment, wherein the illumination source has a known or predetermined spectral composition.

Embodiment 3: The method according to any one of the preceding embodiments, wherein the illumination source is adapted to outshine in brightness ambient light.

Embodiment 4: The method according to any one of the preceding embodiments, wherein the first image and the second image are captured prior to an application of the sample.

Embodiment 5: The method according to any one of the preceding embodiments, wherein the method comprises at least one sample application step, wherein in the sample application step a sample is applied to the test strip, wherein the sample is applied to the test strip prior to steps a) and/or b).

Embodiment 6: The method according to any one of the preceding embodiments, wherein deriving the suitability information in step d) comprises comparing the difference in lighting conditions determined in step c) with at least one threshold value.

Embodiment 7: The method according to the preceding embodiment, wherein, only in case the difference in lighting conditions between the second image and the first image at least equals the threshold value, the suitability information is set to indicate a suitability of the lighting conditions for analyte detection.

Embodiment 8: The method according to any one of the preceding embodiments, wherein the suitability information is set to indicate a suitability of the lighting conditions for subsequent analyte detection only in case at least 80% of light intensity used for illumination of the test strip originates from the illumination source.

Embodiment 9: The method according to any one of the preceding embodiments, wherein the method further comprises checking and/or evaluating whether or not the illumination source provides for sufficient illumination intensity.

Embodiment 10: The method according to any one of the preceding embodiments, wherein the camera is the camera of a mobile communications device.

Embodiment 11: The method according to any one of the preceding embodiments, wherein the illumination source of the mobile device comprises at least one light-emitting diode integrated in the mobile device.

Embodiment 12: A detection method for detecting an analyte in a sample by using a camera of a mobile device, the method comprising:
i) Evaluating lighting conditions by using the method for evaluating a suitability of lighting conditions according to any one of the preceding embodiments;
ii) if the suitability information on the suitability of the lighting conditions indicates the lighting conditions to be suitable for analyte detection, performing the following steps:
A) providing at least one test strip for detecting the analyte in the sample, the test strip having at least one test field comprising at least one test chemical for performing an optical detection reaction in the presence of the analyte;
B) applying at least one sample to the test field of the test strip;
C) capturing at least one image of the test field by using the camera, wherein during said capturing the illumination source of the mobile device is turned on; and
D) determining, from the image captured in step C), the analyte concentration in the sample.

Embodiment 13: The detection method according to the preceding embodiment, wherein step D) comprises analyzing the color of a spot on the test field of the test strip, said spot at least partially comprising the sample.

Embodiment 14: The detection method according to any one of the two preceding embodiments, wherein step C) comprises providing visual indication for the user to position the test strip relative to the camera such that the test field at least partially is located in a target area.

Embodiment 15: The detection method according to any one of the two preceding embodiments, wherein after step D) the lighting conditions are evaluated by using the method for evaluating a suitability of lighting conditions according to any one of the preceding embodiments, wherein the determined analyte concentration is rejected if the suitability information on the suitability of the lighting conditions indicates the lighting conditions not to be suitable for analyte detection.

Embodiment 16: A computer program comprising program means for performing the method for evaluating a suitability of lighting conditions according to one of the preceding embodiments referring to a method for evaluating a suitability of lighting conditions while the computer program is being executed on a computer or on a computer network, specifically on a processor of the mobile device.

Embodiment 17: A computer program comprising program means for performing the detection method according to one of the preceding embodiments referring to a detection method while the computer program is being executed on a computer or on a computer network, specifically on a processor of the mobile device.

Embodiment 18: A mobile device, comprising:
at least one camera;
at least one illumination source; and
at least one processor, comprising program means for performing the method for evaluating a suitability of lighting conditions according to one of the preceding embodiments referring to a method for evaluating a suitability of lighting conditions.

Embodiment 19: The mobile device according to the preceding embodiment, wherein the processor further comprises program means for performing the detection method according to any one of the preceding embodiments referring to a detection method.

Embodiment 20: The mobile device according to any one of the two preceding embodiments, wherein the mobile device is a mobile communications device.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
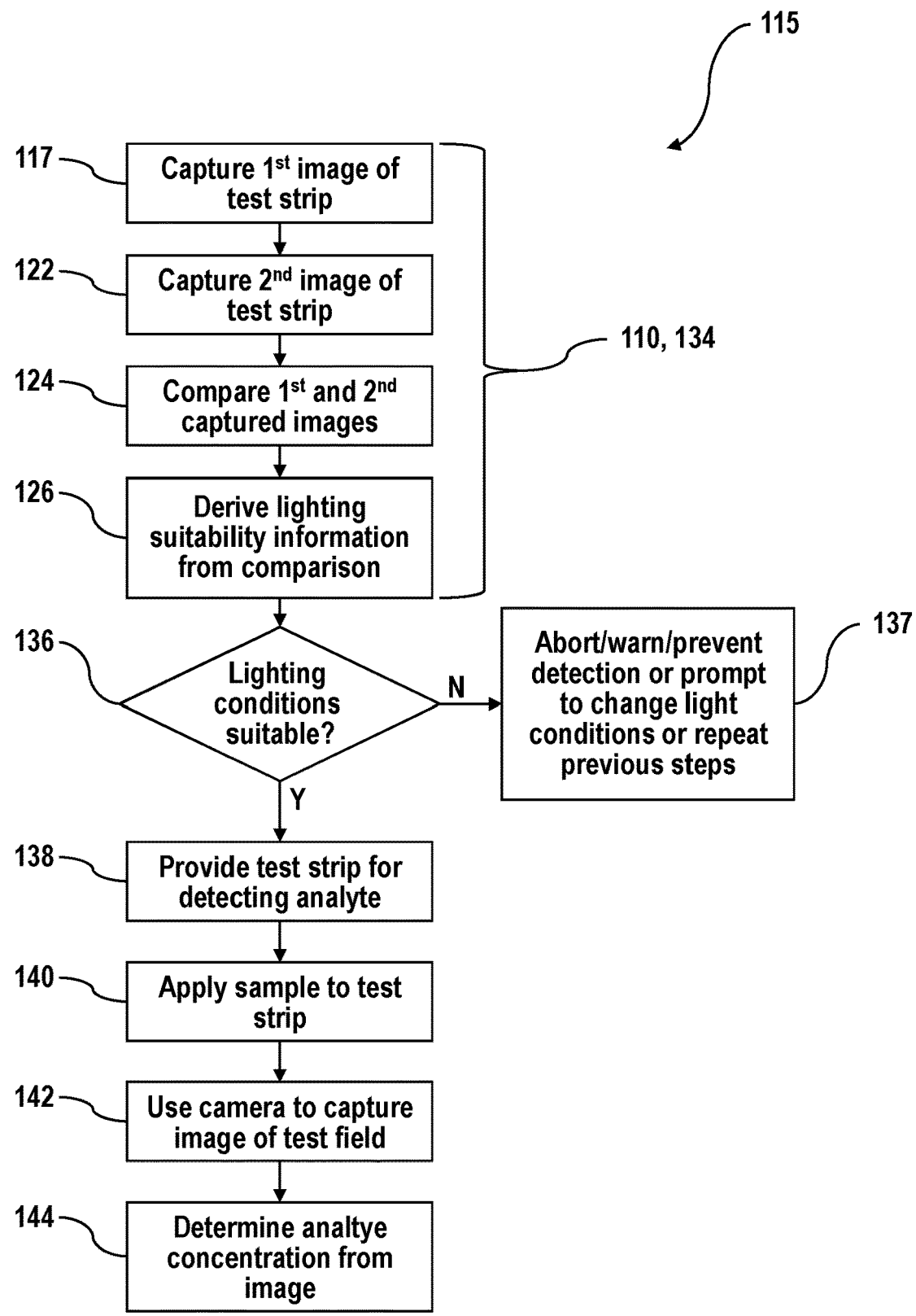
FIG. 1 shows a flow chart of a method for evaluating a suitability of lighting conditions and a method for detecting an analyte.

FIG. 1 shows a flow chart of a method 110 for evaluating a suitability of lighting conditions for detecting an analyte in a sample using a camera 112 of a mobile device 114 and of a method for detecting an analyte 115. The method 110 for evaluating the suitability comprises the following steps:
   a) (denoted with reference number 117) capturing at least one first image of at least one test strip 116, wherein the test strip 116 is adapted for detecting the analyte in the sample, the test strip 116 having at least one test field 118 comprising at least one test chemical for performing an optical detection reaction in the presence of the analyte, wherein, during the capturing of the first image, an illumination source 120 of the mobile device 114 is turned off;
   b) (denoted with reference number 122) capturing at least one second image of the test strip 116, wherein, during the capturing of the second image, the illumination source 120 of the mobile device 114 is turned on;
   c) (denoted with reference number 124) comparing the first and second images captured in steps a) 117 and b) 122, thereby determining a difference in lighting conditions between the first image and the second image; and
   d) (denoted with reference number 126) deriving at least one suitability information from the comparison in step c) 124, wherein the suitability information comprises information on a suitability of the lighting conditions for analyte detection.

Figure 2:
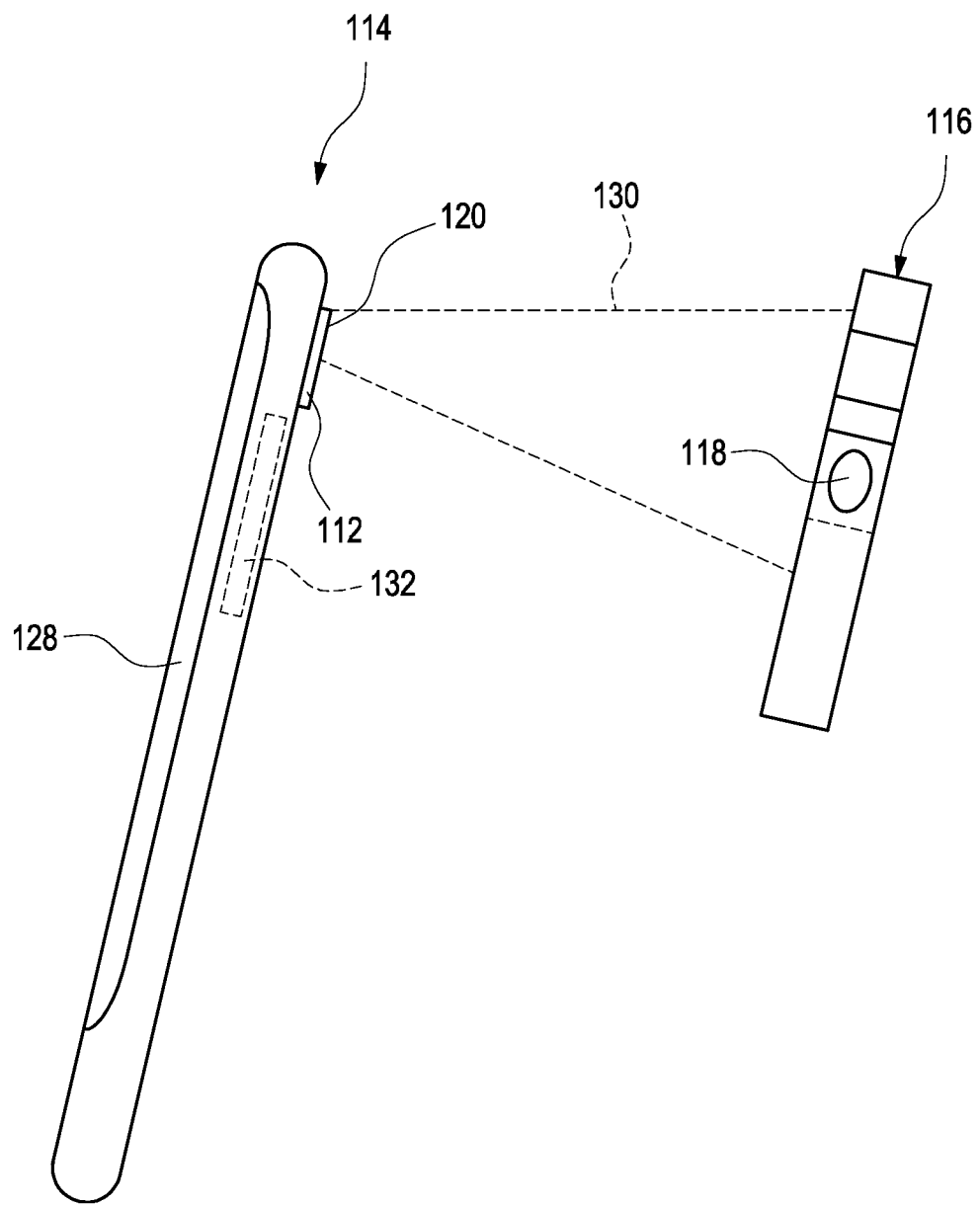
FIG. 2 shows a perspective view of an embodiment of a mobile device for performing the method for evaluating the suitability of lighting conditions.

In FIG. 2 the mobile device 114 for performing the method 110 for evaluating the suitability of lighting conditions is shown in a perspective view. The mobile device 114 may be a mobile electronics device, more specifically a mobile communication device such as a cell phone or smart phone. Additionally or alternatively, the mobile device 114 may also refer to a tablet computer or another type of portable computer having at least one camera. Furthermore, the at least one test strip 116 is shown. The test strip 118 has the test field 118 containing at least one test chemical for detecting the at least one analyte. The test strip 116, as an example, may comprise at least one substrate, such as at least one carrier, with the at least one test field 118 applied thereto or integrated therein.

The mobile device 114 comprises the at least one camera 112. The camera 112 may comprise at least one camera chip, not shown here, such as at least one CCD chip and/or at least one CMOS chip configured for recording images. The camera 112 generally may comprise a one-dimensional or two-dimensional array of image sensors, such as pixels. The camera 112 may be a camera of a mobile communications device. The camera 112 specifically may be a color camera. The camera 112 may be adapted to generate color values for at least three colors, e.g., for red (R), green (G), blue (B). As an example, each pixel of the camera chip may have three or more different color sensors, such as color recording pixels like one pixel for R, one pixel for G, one pixel for B.

The method 110 for evaluating the suitability of lighting conditions may comprise determining an impact of ambient light on image capturing with the camera 112 of the mobile device 114. For example, the suitability information may comprise information about sufficiency of light intensity originating from the illumination source 120 of the mobile device 114 for illuminating the test strip 116. Specifically, the suitability information may comprise information about sufficiency of light intensity originating from the illumination source 120 of the mobile device 114 for illuminating the test strip 116 in relation to and/or in comparison to ambient light intensities and/or ambient light conditions. The ambient light may be generated and/or provided by artificial light sources such as room light, e.g., lamps, and/or natural light sources such as the sun, the moon, starlight, lightning. The lighting conditions may depend on time, in particular day or night time. The lighting condition may depend on location, in particular if the image is captured outdoor or indoor or on geographical location. In particular for outdoor measurements, the lighting conditions may depend on weather conditions. For indoor measurements, the lighting conditions may depend on room lightings, which may differ dependent on activity such as in homes, supermarkets, theaters, etc.

The illumination source 120 may comprise at least one light-emitting diode integrated in the mobile device 114. In particular, the illumination source 120 may be a backlighting of the mobile device 114, in particular of the mobile phone. The mobile device 114 may comprise further illumination devices such as at least one illumination source illuminating at least one display 128 and/or the display 128 may be designed as further illumination source itself.

The illumination source 120 may have two states, an on-state in which it generates light beam for illuminating the test strip 116 and an off-state in which the illumination source 120 is off and no light is generated. As outlined above, in step a) 117 a first image is captured wherein the illumination source 120 of the mobile device 114 is turned off. This may allow capturing an image comprising light intensities of ambient light sources only and independent from illumination provided by the illumination source 120 of the mobile device 114. In step b) 122 the illumination source 120 is turned on such that it may be possible to determine the second image comprising illumination intensities from both ambient light and from the illumination by the illumination source 120 of the mobile device 114.

The light-emitting diode integrated in the mobile device 114 may comprise at least one white light LED. The white light LED may be controlled using a short current pulse such that the white light LED may be adapted to generate a bright flash of light. The illumination source 120 may be adapted to illuminate the test strip 116 all the time during capturing of the image. In contrast to electron flashes, flash duration of the white light LED may take several 100 ms. This may allow that the illumination source 120 illuminates the test strip 116 all the time during capturing of the image in a flash-mode of the LED. Alternatively, the LED may be adapted to be permanently illuminating the test strip in a non-flash mode, in which the LED is adapted to generate continuously at least one light beam for illuminating the test strip 116.

The illumination source 120 may be adapted to outshine in brightness (brighter than) ambient light. The illumination source 120 may be an essentially dominant light source when capturing the image in step b) 122 of the test strip 116. Illuminance of flashes generated by the white light LED used in mobile devices may be from 80 to 300 lux at an object distance of 1 m. Thus, at an object distance of 0.1 m, illuminance of flashes generated by the white light LED may be from 8000 to 30000 lux. For comparison, full daylight may have 10752 lux, an overcast day may have 1075 lux, a very dark day may have 107 lux, and twilight may have 10.8 lux, see Recommended Light Levels published by the National Optical Astronomy Observatory. The illumination source 120 may be adapted to generate at least one light beam 130 for illuminating the test strip 116 comprising light intensities above light intensities of ambient light. The light intensities of the light beam 130 generated by the illumination source 120 may exceed the light intensities of ambient light by a factor of two, preferably by a factor of 10 and more preferably by a factor of 100.

Step c) 124 comprises comparing the first and second images captured in steps a) 117 and b) 122, thereby determining a difference in lighting conditions between the first image and the second image. As outlined above, each pixel of the camera chip may have three or more different color sensors, such as color recording pixels like one pixel for red (R), one pixel for green (G) and one pixel for blue (B). For example, the camera 112 may comprise at least one Bayer sensor. The camera chip may be adapted to generate at least one sensor signal for each of the R, G, B channels. The camera chip may be adapted to determine an intensity spectrum of the respective R, G, B channel. The camera 112 may be adapted to capture the first and second images in steps a) 117 and b) 122 in at least one color channel, in particular at least one color channel selected from the group consisting of R channel, G channel and B channel. The camera 112 may be adapted to capture the first and second images in steps a) 117 and b) 122 in each of the color channels. The mobile device 114 comprises at least one processor 132. The camera 112 and/or the processor 132 may be adapted to determine from the first image at least one first intensity distribution and from the second image at least one second intensity distribution for at least one of the color channels. Preferably, a first intensity distribution and a second intensity distribution may be determined for each of the color channels. For at least one color channel, the camera 112 and/or the processor 132 may be adapted to determine from the respective first intensity distribution a first intensity spectrum of the respective color channel and from the respective second intensity distribution a second intensity spectrum of the respective color channel. For example, the comparing may comprise determining a difference between the first intensity distribution and the second intensity distribution of at least one of the color channels. Specifically, for the R, G and B channels the difference $\Delta$ may be determined by $$\Delta_{color} = I_{color}^{LEDON} - I_{color}^{LEDOFF},$$

with color=R, G, B, wherein $\Delta_{color}$ is the difference in the respective color channel, $I_{color}^{LEDON}$ is the intensity distribution of the second image of the respective color channel and $I_{color}^{LEDOFF}$ is the intensity distribution of the first image of the respective color channel. Additionally or alternatively, the comparing may comprise determining a quotient by dividing the first intensity distribution and the second intensity distribution and/or by dividing multiples and/or dividing linear combinations of the first intensity distribution and the second intensity distribution for at least one of the color channels. Specifically, for the R, G and B channels the quotient may be determined by $$Q_{color} = I_{color}^{LEDON} / I_{color}^{LEDOFF},$$

with color=R, G, B, wherein $Q_{color}$ is the quotient in the respective color channel, $I_{color}^{LEDON}$ is the intensity distribution of the second image of the respective color channel and $I_{color}^{LEDOFF}$ is the intensity distribution of the first image of the respective color channel. The processor 132 may comprise computing means adapted for comparing the first and second images.

The illumination source 120 of the mobile device 114 may have a known or predetermined spectral composition. In particular, at least one distribution of light intensities as a function of wavelength for each of the R, G, B channels may be known or predetermined. Specifically, an emission spectrum of the white light LED may be known or may be determined empirically. The spectral composition may be stored in a table or a lookup table and may be determined, e.g., empirically and may, as an example, be stored in at least one data storage device of the mobile device, e.g., by software, specifically by the app downloaded from an app store or the like. Since the spectral composition of the illumination source 120 is known or is predetermined, it may be possible to determine the amount of light intensity used for illumination of the test strip 116 which originates from the illumination source 120.

The first image and the second image may be captured prior to an application of the sample. Additionally or alternatively, the method may comprise at least one sample application step, wherein in the sample application step a sample may be applied to the test strip 116. Specifically, the sample may be applied to the test strip 116 prior to steps a) 117 and/or b) 122.

Step d) 126 comprises deriving the at least one suitability information from the comparison in step c) 124. Deriving the suitability information in step d) 126 may comprise comparing the difference in lighting conditions determined in step c) 124 with at least one threshold value. Only in case the difference in lighting conditions between the second image and the first image at least equals the threshold value, the suitability information may be set to indicate a suitability of the lighting conditions for analyte detection. The threshold value may depend on ambient light conditions. For example, the user and/or the processor 132 may be adapted to adjust and/or select the threshold value dependent on ambient light conditions. The threshold value may be stored in a table or a lookup table and may be determined, e.g., empirically and may, as an example, be stored in at least one data storage device of the mobile device, e.g., by software, specifically by the app downloaded from an app store or the like. For example, the suitability information may be set to indicate a suitability of the lighting conditions for subsequent analyte detection only in case at least 80% of light intensity used for illumination of the test strip 116 originates from the illumination source 120. For example, the suitability information may be set to indicate a suitability of the lighting conditions for subsequent analyte detection only in case 90% of light intensity used for illumination of the test strip 116 originates from the illumination source 120.

Figure 3:
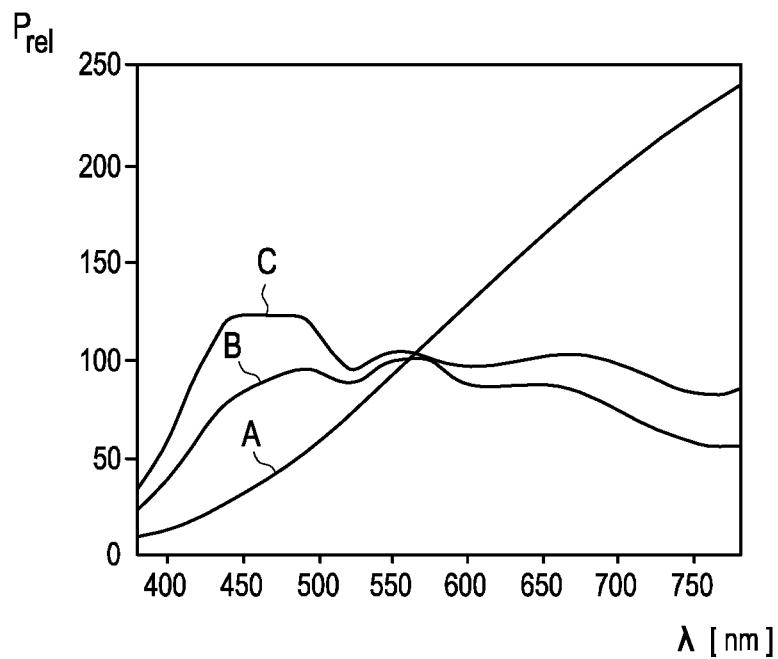
FIGS. 3A to 3G show relative spectral power distributions of standard illuminant and experimental results of impact of ambient light on camera image.
Figure 3:
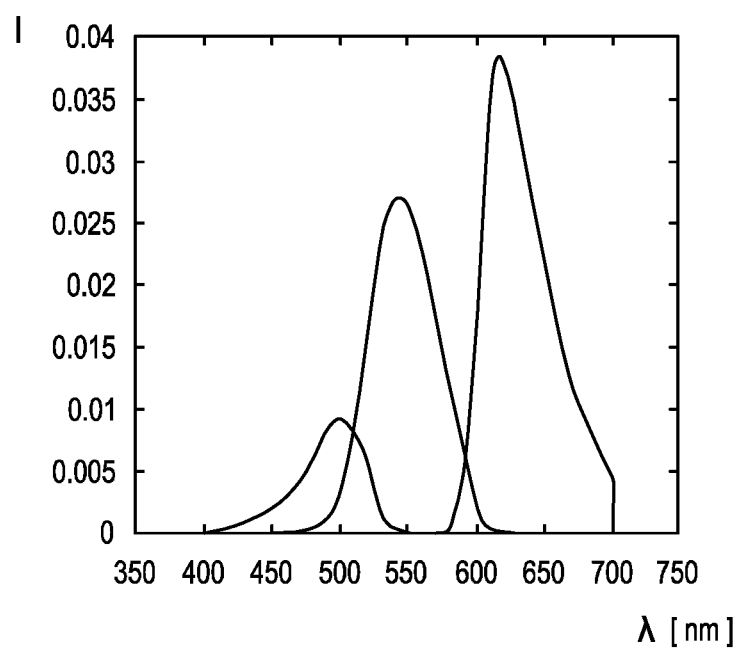
Figure 3:
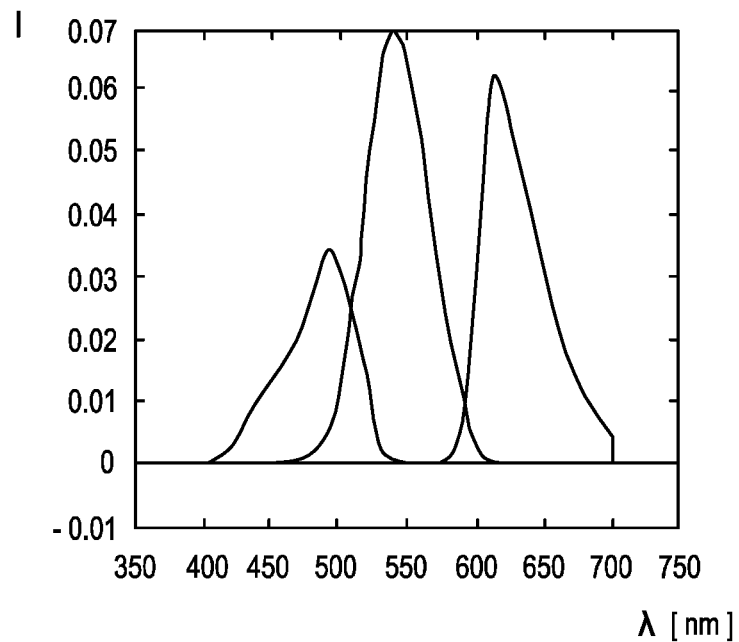
Figure 3:
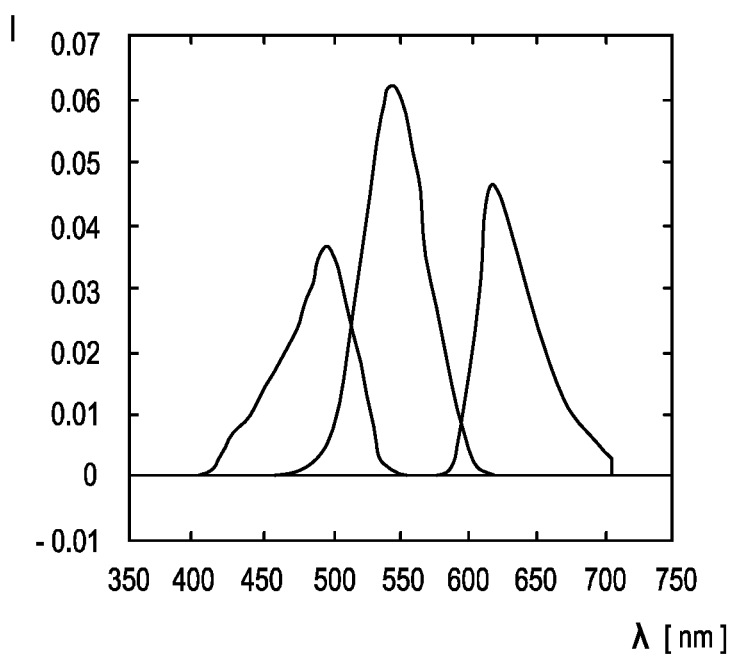
Figure 3:
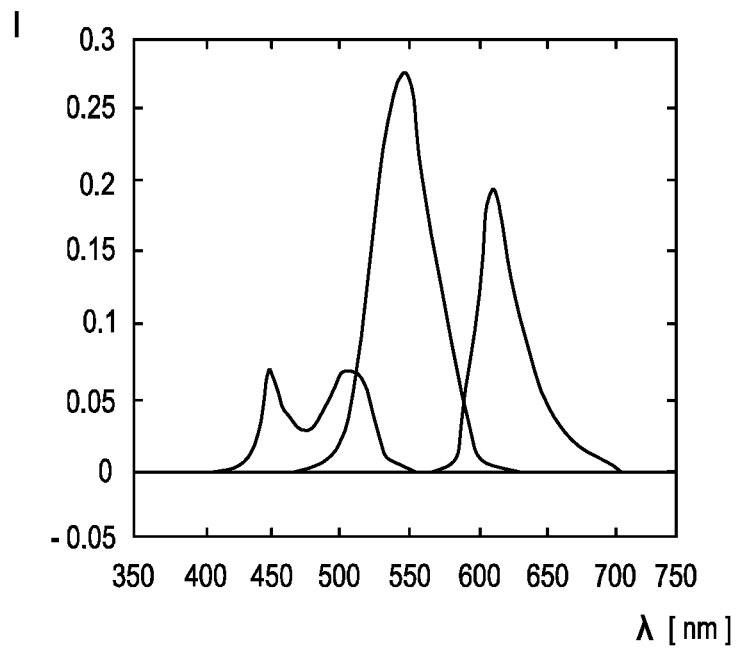
Figure 3:
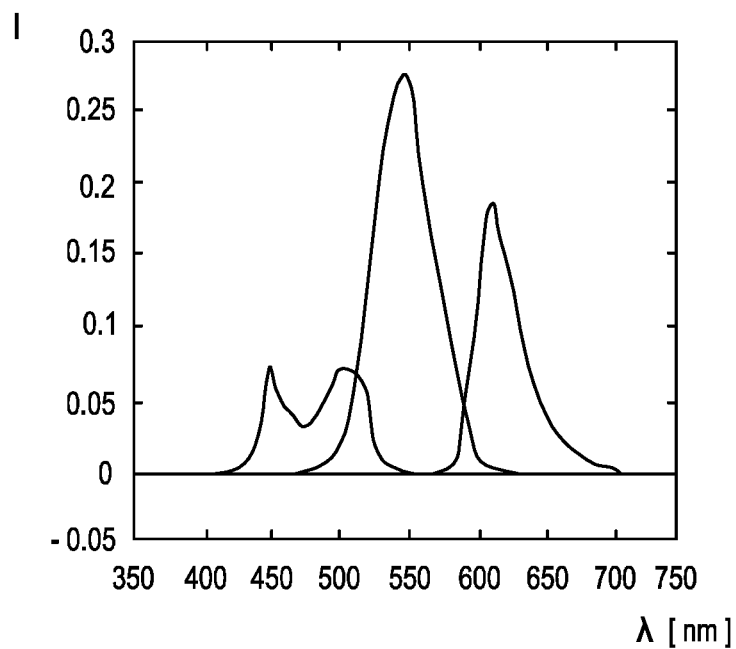
Figure 3:
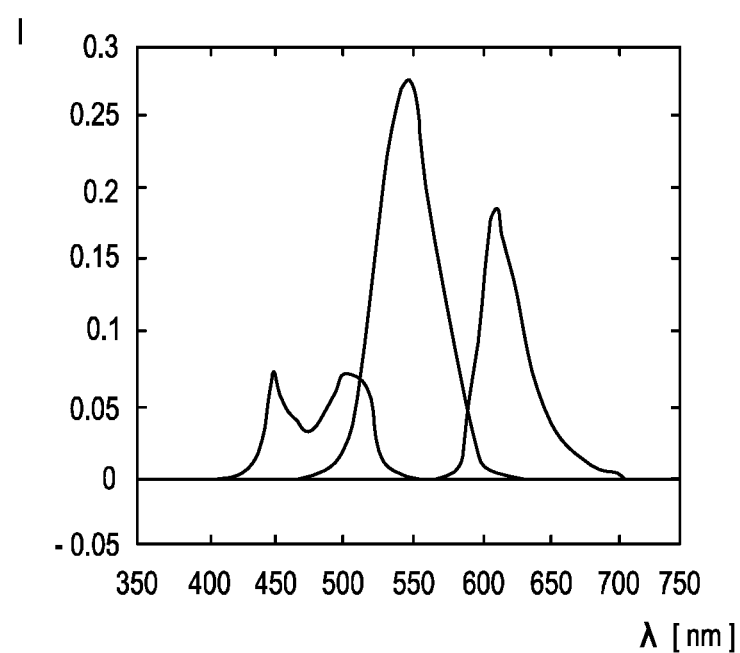

FIG. 3A shows a relative power distribution of CIE standard illuminants A, B, C from 380 nm to 780 nm, see, e.g., Standard Illuminant entry on Wikipedia.org. FIG. 3B shows intensity I of determined RGB-signals as a function of wavelength λ in nm for a blood sample of 100 mg/dl being illuminated with standard illuminant A. FIG. 3C shows intensity I of the determined RGB-signals as a function of wavelength λ in nm for a blood sample of 100 mg/dl being illuminated with standard illuminant B. FIG. 3D shows intensity I of the determined RGB-signals as a function of wavelength λ in nm for a blood sample of 100 mg/dl being illuminated with standard illuminant C. It is observed that the intensity of determined RGB-signals as a function of wavelength change depending on the illumination by the respective illuminant A, B or C. FIG. 3E shows intensity I of the determined RGB-signals as a function of wavelength λ in nm for a blood sample of 100 mg/dl, wherein the sample is illuminated with 10% light intensity from standard illuminant A and with 90% light intensity from illumination source 120, in this case a light emitting diode of a Samsung Galaxy® J7 smartphone. It is observed that the intensity of determined RGB-signals as a function of wavelength is independent on illumination by the respective illuminant. The illumination originating from the illumination source 120 dominates the lighting condition.

Referring to FIG. 1, the detection method 115 comprises step i) 134, wherein lighting conditions by using the method for evaluating the suitability of lighting conditions are evaluated. The detection method 115 comprises step ii) 136, wherein, if the suitability information on the suitability of the lighting conditions indicates the lighting conditions to be suitable for analyte detection, the following steps are performed:

A) (indicated with reference number 138) providing the at least one test strip 116 for detecting the analyte in the sample, the test strip 116 having the at least one test field 118 comprising at least one test chemical for performing an optical detection reaction in the presence of the analyte;

B) (indicated with reference number 140) applying at least one sample to the test field 118 of the test strip 116;

C) (indicated with reference number 142) capturing at least one image of the test field 118 by using the camera 112, wherein during said capturing the illumination source 120 of the mobile device is turned on; and D) (indicated with reference number 144) determining, from the image captured in step C), the analyte concentration in the sample.

Step C) 142 may comprise providing visual indication for the user to position the test strip 116 relative to the camera 112 such that the test field 118 at least partially is located in a target area. The visual indication such as visual guidance may be given to the user prior to capturing the image. The visual indication may comprise at least one instruction such as a text message and/or a graphical instruction. For example, the visual indication may comprise a visualization of the test strip 116 or parts of the test strip 116 such as a contour and/or outline of the test strip 116. The visual indication may comprise an outline of the test strip 116 or a reference region on the test strip 116, for example a frame which corresponds to a shape of the test strip 116, superimposed on the display 128 of the mobile device 114, providing visual guidance for positioning the camera 112 relative to the test strip 116.

In case the evaluating of lighting conditions in step i) 134 is not set to indicate that the lighting conditions are suitable, the mobile device 114 may be adapted to abort and/or to prevent detecting the analyte in the sample. Additionally or alternatively, in case the evaluating of lighting conditions in step i) 134 is not set to indicate that the lighting conditions are suitable, the mobile device 114 may be adapted to generate at least one warning. Additionally or alternatively, in case the evaluating of lighting conditions in step i) 134 is not set to indicate that the lighting conditions are suitable, the mobile device 114 may be adapted to repeat step i) 134. Additionally or alternatively, in case the evaluating of lighting conditions in step i) is not set to indicate that the lighting conditions are suitable, the mobile device 114 may be adapted to generate at least one prompt to the user to change ambient light conditions, for example to move to a different location and/or to switch off disturbing light sources. See step 137.

After step D) 144 the lighting conditions may be evaluated by using the method 110 for evaluating a suitability of lighting conditions as described above. The determined analyte concentration may be rejected if the suitability information on the suitability of the lighting conditions indicates the lighting conditions not to be suitable for analyte detection. The mobile device 114 may be adapted to generate at least one error message if the suitability information on the suitability of the lighting conditions indicates the lighting conditions have not been suitable during analyte detection. The mobile device 114 may be adapted to generate a warning to the user, such as a visual warning on the display 128 of the mobile device 114 and/or at least one acoustical warning.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 method for evaluating a suitability of lighting conditions
112 Camera
114 mobile device
115 method for detecting an analyte
116 test strip
117 step a)
118 test field
120 illumination source
122 step b)
124 step c)
126 step d)
128 Display
130 light beam
132 Processor
134 step i)
136 step ii)
138 step A)
140 step B)
142 step C)
144 step D)

What is claimed is:

1. A method of evaluating suitability of lighting conditions for detecting an analyte in a sample using a mobile device having a camera, the method comprising:

a) providing a test strip configured for detecting the analyte in the sample and having at least one test field with a test chemical for an optical detection reaction;

b) capturing a first image of the test strip while an illumination source of the mobile device is turned off;
c) capturing a second image of the test strip while the illumination source is turned on, wherein the illumination source generates illumination having a known or predetermined spectral composition;
d) applying a sample to the test strip prior to step c);
e) comparing the first and second images and thereby determining a difference in lighting conditions between the first image and the second image, wherein the camera captures the images in steps b) and c) in at least one color channel and the camera and/or a processor of the mobile device determines first and second intensity distributions, respectively, for the at least one color channel associated with the first and second images, wherein the comparing the first and second images comprises comparing the first intensity distribution and the second intensity distribution of the at least one color channel;
f) determining an intensity of the illumination which originates from the illumination source used for illumination of the test strip when capturing the second image as a function of the known or predetermined spectral composition and wherein the known or predetermined spectral composition of the illumination source is obtained before capturing an image of the test strip of step a) with the mobile device;
g) deriving suitability information of the lighting conditions for analyte detection from the comparison in step e) and the determination of step f); and
h) determining that the lighting conditions are suitable for subsequent analyte detection using the second image when at least 70% of light intensity used for illumination of the test strip in the second image originates from the illumination source.

2. The method according to claim 1, wherein the illumination source is adapted to shine brighter than ambient light.

3. The method according to claim 1, wherein the first image is captured after applying the sample to the test strip in step d).

4. The method according to claim 1, wherein deriving the suitability information comprises comparing the difference in lighting conditions determined in step e) with a threshold value.

5. The method according to claim 1, wherein step h) comprises indicating that the lighting conditions are suitable for subsequent analyte detection when at least 80% of light intensity used for illumination of the test strip originates from the illumination source.

6. The method according to claim 1, further comprising checking and/or evaluating whether the illumination source provides sufficient illumination intensity.

7. The method according to claim 1, wherein the illumination source comprises at least one light-emitting diode integrated therein.

8. The method of claim 1, further comprising, when the suitability information indicates the lighting conditions are suitable for analyte detection, determining the analyte concentration in the sample using the second image.

9. A non-transitory computer readable medium having stored thereon computer executable instructions for performing the method of claim 1.

10. The non-transitory computer readable medium of claim 9, comprising a mobile device.

11. A mobile device, comprising:
a camera;
an illumination source; and
a processor or computer readable medium having stored thereon computer executable instructions for performing the method of claim 1.

12. The mobile device according to claim 11, wherein the mobile device is a mobile communications device.

13. The method according to claim 1, wherein the illumination of the test strip in the second image being assessed in step h) was provided by both ambient light and light originating from the illumination source.

14. The method according to claim 8, wherein the illumination of the test strip in the second image used to determine the analyte concentration was provided by both ambient light and light originating from the illumination source.

15. The method according to claim 1, further comprising a step of providing a visual indication with the mobile device to indicate a location for positioning the test strip relative to the camera when capturing the first and second images of the test strip wherein the visual indication is an outline of the test strip or a reference region of the test strip and is superimposed on a display of the mobile device.

16. The method according to claim 1, wherein the known or predetermined spectral composition is stored in a data storage device and the step of determining the intensity of the illumination which originates from the illumination source is performed as a function of the known or predetermined spectral composition stored on the data storage device.

17. The method according to claim 1, wherein the known or predetermined spectral composition is a known spectral composition of a standard illuminant.

18. The method according to claim 1, wherein the illumination source comprises at least one white light LED, wherein the at least one white light LED is controlled using a short current pulse to illuminate the test strip continuously during capture of the second image and wherein illuminance of flashes generated by the at least one white light LED are from 80 to 300 lux at an object distance of 1 m.

* * * * *